United States Patent [19]
Matsuda et al.

[11] Patent Number: 6,111,111
[45] Date of Patent: Aug. 29, 2000

[54] INTERMEDIATES FOR PRODUCING PYRIDINE DERIVATIVES

[75] Inventors: Hideki Matsuda; Goro Asanuma; Takanobu Shin; Manzo Shiono; Shigeki Kikuyama, all of Okayama, Japan

[73] Assignee: Kuraray Co., Ltd., Kurashiki, Japan

[21] Appl. No.: 09/175,958

[22] Filed: Oct. 21, 1998

[30] Foreign Application Priority Data

| Oct. 23, 1997 | [JP] | Japan | ................................. | 9-291075 |
| Mar. 19, 1998 | [JP] | Japan | ................................. | 10-064862 |
| Aug. 4, 1998 | [JP] | Japan | ................................. | 10-219943 |

[51] Int. Cl.⁷ .................... C07D 491/048; C07D 495/04
[52] U.S. Cl. ............................ 546/114; 546/115
[58] Field of Search ................... 546/113, 114, 546/115

[56] References Cited

PUBLICATIONS

Dellouve–Courillon et al, Tetrahedron, vol. 46, No. 9, p. 3245, 3251, 3262 and 3263, 1990.

*Primary Examiner*—Bernard Dentz
*Attorney, Agent, or Firm*—Oblon, Spivak, McClelland, Maier & Neustadt, P.C.

[57] ABSTRACT

A pyridine alcohol derivative represented by General Formula III

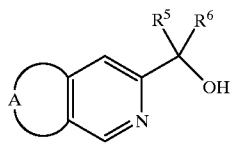
(III)

(where A represents a divalent organic group which may contain one to three oxygen atoms, nitrogen atoms and/or sulfur atoms, wherein A may form a 5-, 6-, 7-, or 8-membered ring together with two bonded carbon atoms, where said ring may form a condensed ring with one or more additional rings; $R^5$ represents a hydrogen atom, —$CHR^1R^2$, or an alkenyl group, an aryl group or an aralkyl group which may be substituted; $R^1$ and $R^2$ each independently represent a hydrogen atom or a hydrocarbon group which may be substituted; and $R^6$ represents a hydrogen atom, an alkyl group, an alkenyl group, an aryl group or an aralkyl group which may be substituted), is produced by:

reacting a pyridine ester derivative represented by General Formula I-1

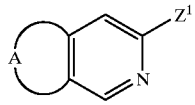

(I-1)

(where $Z^1$ represents —COX; X represents an alkoxyl group, an alkenyloxy group, an aryloxy group or an aralkyloxy group which may be substituted; and A is the same as above)

with a reducing agent, an alkylating agent, an alkenylating agent, an arylating agent or an aralkylating agent to obtain a pyridine carbonyl derivative represented by General Formula II

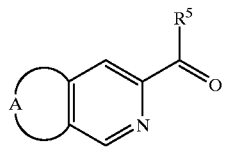
(II)

(where A and $R^5$ are the same as above); and reacting the resulting pyridine carbonyl derivative with a reducing agent, an alkylating agent, an alkenylating agent, an arylating agent or an aralkylating agent to obtain the pyridine alcohol derivative of the General Formula III.

3 Claims, No Drawings

INTERMEDIATES FOR PRODUCING PYRIDINE DERIVATIVES

BACKGROUND OF THE INVENTION

1. Field of the Invention

The present invention relates to methods for producing pyridine derivatives, and to intermediates in the synthesis thereof. The pyridine derivatives produced by the present invention are useful as intermediates in the synthesis of compounds having a pyridine skeleton in the molecule, such as furopyridine derivatives having antiviral activity (see WO 96/35678).

2. Description of the Related Art

Several methods have been disclosed in the past as methods for the synthesis of condensed pyridines such as furopyridines (see Heterocycles, 45(5) (1997), p. 975), but the only known methods for producing 5-substituted furo[2,3-c]pyridines which can be converted to the aforementioned furopyridine derivatives having antiviral activity are methods in which synthesis is achieved through multiple stages using 2-chloro-3-hydroxypyridine as the starting material (see WO 96/35678), and methods in which furfural oxime as the starting material is made into 5-substituted furo[2,3-c]pyridine-N-oxide as a result of ring formation by the Aza Diels-Alder reaction and subsequent dehydrogenation (see Tetrahedron Lett., 32, 3199(1991)).

Problems in the former of the aforementioned methods, however, are the large number of steps as well as the expensive starting materials and reaction agents, while the latter method needs expensive dehydrogenating agents such as 2,3-dichloro-5,6-dicyano-p-benzoquinone (DDQ), and needs the reduction of the pyridine oxide to pyridine, and hence both methods cannot be considered to be industrially useful.

SUMMARY OF THE INVENTION

An object of the present invention is to provide methods in which pyridine derivatives, that allow condensed pyridines such as furopyridine derivatives to be readily produced, can be manufactured with good yields in an industrially useful manner under moderate conditions.

Another object of the present invention is to provide a synthetic intermediate and its method of production giving an industrially useful method for producing the aforementioned pyridine derivatives.

The aforementioned objects have been achieved in the following present invention.

The present invention provides a method for producing a pyridine alcohol derivative represented by General Formula III

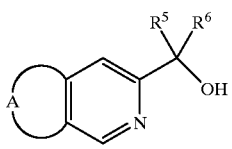

(III)

(where A represents a divalent organic group which may contain one to three oxygen atoms, nitrogen atoms and/or sulfur atoms, wherein A may form a 5-, 6-, 7-, or 8-membered ring together with two bonded carbon atoms, and said ring may form a condensed ring with one or more additional rings; $R^5$ represents a hydrogen atom, —$CHR^1R^2$, or an alkenyl group, an aryl group or an aralkyl group which may be substituted; $R^1$ and $R^2$ each independently represent a hydrogen atom or a hydrocarbon group which may be substituted; and $R^6$ represents a hydrogen atom, an alkyl group, an alkenyl group, an aryl group or an aralkyl group which may be substituted), wherein the method comprises:

reacting a pyridine ester derivative represented by General Formula I-1

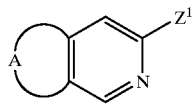

(I-1)

(where $Z^1$ represents —COX; X represents an alkoxyl group, an alkenyloxy group, an aryloxy group or an aralkyloxy group which may be substituted; and A is the same as above)

with a reducing agent, an alkylating agent, an alkenylating agent, an arylating agent or an aralkylating agent to obtain a pyridine carbonyl derivative represented by General Formula II

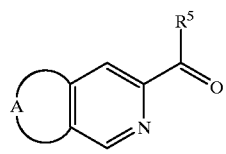

(II)

(where A and $R^5$ are the same as above); and reacting the resulting pyridine carbonyl derivative represented by General Formula II with a reducing agent, an alkylating agent, an alkenylating agent, an arylating agent or an aralkylating agent to obtain the pyridine alcohol derivative of the General Formula III.

The present invention also provides a method for producing a pyridine alcohol derivative represented by General Formula III, wherein the method comprises:

reacting a pyridine carbonyl derivative represented by General Formula II with a reducing agent, an alkylating agent, an alkenylating agent, an arylating agent or an aralkylating agent to obtain the pyridine alcohol derivative of the General Formula III.

The present invention further provides a pyridine carbonyl derivative represented by General Formula II-1

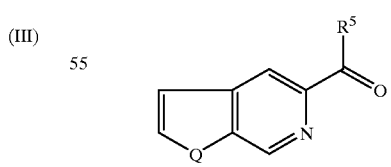

(II-1)

(where $R^5$ represents a hydrogen atom, —$CHR^1R^2$, or an alkenyl group, an aryl group or an aralkyl group which may be substituted; $R^1$ and $R^2$ each independently represent a hydrogen atom or a hydrocarbon group which may be substituted; Q represents a divalent group selected from —ND—, —O—, and —S—; and D represents a hydrogen atom or a hydrocarbon group which may be substituted).

The present invention still further provides a method for producing a pyridine carbonyl derivative represented by General Formula II, wherein the method comprises:

reacting a pyridine ester derivative represented by General Formula I-1 with a reducing agent, an alkylating agent, an alkenylating agent, an arylating agent or an aralkylating agent.

The present invention also provides a method for producing a pyridine alcohol derivative represented by General Formula III, wherein the method comprises:

reacting a pyridine ester derivative represented by General Formula I-1 in the presence of a base with an ester compound represented by General Formula IV

(where $R^1$ and $R^2$ are the same as above; and $R^3$ represents a hydrocarbon group which may be substituted)

to obtain a pyridine β-ketoester derivative represented by General Formula V

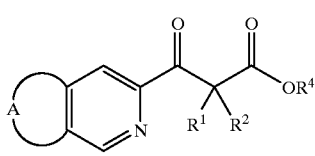

(where $R^1$, $R^2$, and A are the same as above; and $R^4$ is a hydrocarbon group which may be substituted); and hydrolyzing and decarboxylating the resulting pyridine β-ketoester derivative represented by General Formula V to obtain the pyridine carbonyl derivative represented by General Formula II; and reacting the pyridine carbonyl derivative represented by General Formula II with a reducing agent, an alkylating agent, an alkenylating agent, an arylating agent or an aralkylating agent to obtain the pyridine alcohol derivative represented by General Formula III.

The present invention further provides a method for producing a pyridine β-ketoester derivative represented by General Formula V, wherein the method comprises:

reacting a pyridine ester derivative represented by General Formula I-1 with in the presence of a base with an ester compound represented by General Formula IV to obtain the pyridine β-ketoester derivative represented by General Formula V.

The present invention still further provides a pyridine β-ketoester derivative represented by General Formula V-1

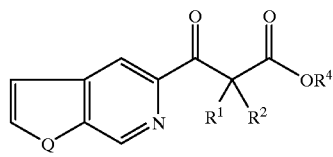

(where $R^1$ and $R^2$ each independently represent a hydrogen atom or a hydrocarbon group which may be substituted; $R^4$ represents a hydrocarbon group which may be substituted; Q represents a divalent group selected from —ND—, —O—, and —S—; and D represents a hydrogen atom or a hydrocarbon group which may be substituted).

The present invention also provides a method for producing a pyridine carbonyl derivative represented by General Formula II, wherein the method comprises:

hydrolyzing and decarboxylating a pyridine β-ketoester derivative represented by General Formula V to obtain the pyridine carbonyl derivative represented by General Formula II.

The present invention also provides a pyridine ester derivative represented by General Formula I-1'

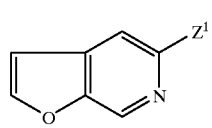

(where $Z^1$ represents —COX; and X represents an alkoxyl group, alkenyloxy group, aryloxy group or aralkyloxy group which may be substituted).

The present invention also provides a sulfonylpyridine derivative represented by General Formula I-2

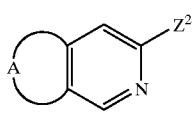

(where $Z^2$ represents an organic sulfonyl group represented by —SO$_2$R$^9$; R$^9$ represents an organic group; and A represents a divalent organic group which may contain one to three oxygen atoms, nitrogen atoms and/or sulfur atoms, wherein A may form a 5-, 6-, 7-, or 8-membered ring together with two bonded carbon atoms, and said ring may form a condensed ring with one or more additional rings).

The present invention also provides a method for producing a pyridine derivative represented by General Formula I

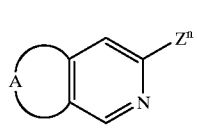

(where n of $Z^n$ is 1 or 2; $Z^1$ represents —COX; X represents an alkoxyl group, an alkenyloxy group, an aryloxy group or an aralkyloxy group which may be substituted; $Z^2$ represents an organic sulfonyl group represented by the formula, —SO$_2$R$^9$; R$^9$ is an organic group; and A represents a divalent organic group which may contain one to three oxygen atoms, nitrogen atoms and/or sulfur atoms, wherein A may and form a 5-, 6-, 7-, or 8-membered ring together with two bonded carbon atoms, and said ring may form a condensed ring with one or more additional rings), wherein the method comprises:

reacting an imine derivative represented by General Formula VI

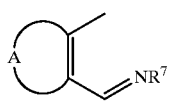

(where $R^7$ is an alkyl group, an alkenyl group, an aryl group or an aralkyl group which may be substituted; and A is the same as above)

with a carbonylating agent represented by General Formula VII

  (VII)

(where $R^8$ is a hydrogen atom, an alkyl group, an alkenyl group, an aryl group, an aralkyl group, an alkoxyl group, an alkenyloxy group, an aryloxy group, an aralkyloxy group or an amino group which may be substituted; and Y represents a leaving group)

and a nitrile derivative represented by General Formula VIII $$Z^n CN \quad (VIII)$$

(where $Z^n$ is the same as above) to obtain the pyridine derivative represented by General Formula I.

The imine derivative represented by General Formula VI may preferably be obtainable by a method comprises:

reacting an aldehyde derivative represented by the General Formula IX

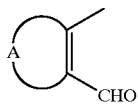  (IX)

(where A is the same as above)
with a primary amine represented by the General Formula X $$R^7 NH_2 \quad (X)$$

(where $R^7$ is the same as above)
to obtain the imine derivative represented by General Formula VI.

These and other objects, features and advantages of the present invention are described in or will become apparent from the following detailed description of the invention.

DETAILED DESCRIPTION OF THE INVENTION

The present invention will be explained in more detail by referring to the following Reaction Scheme.

Reaction Scheme

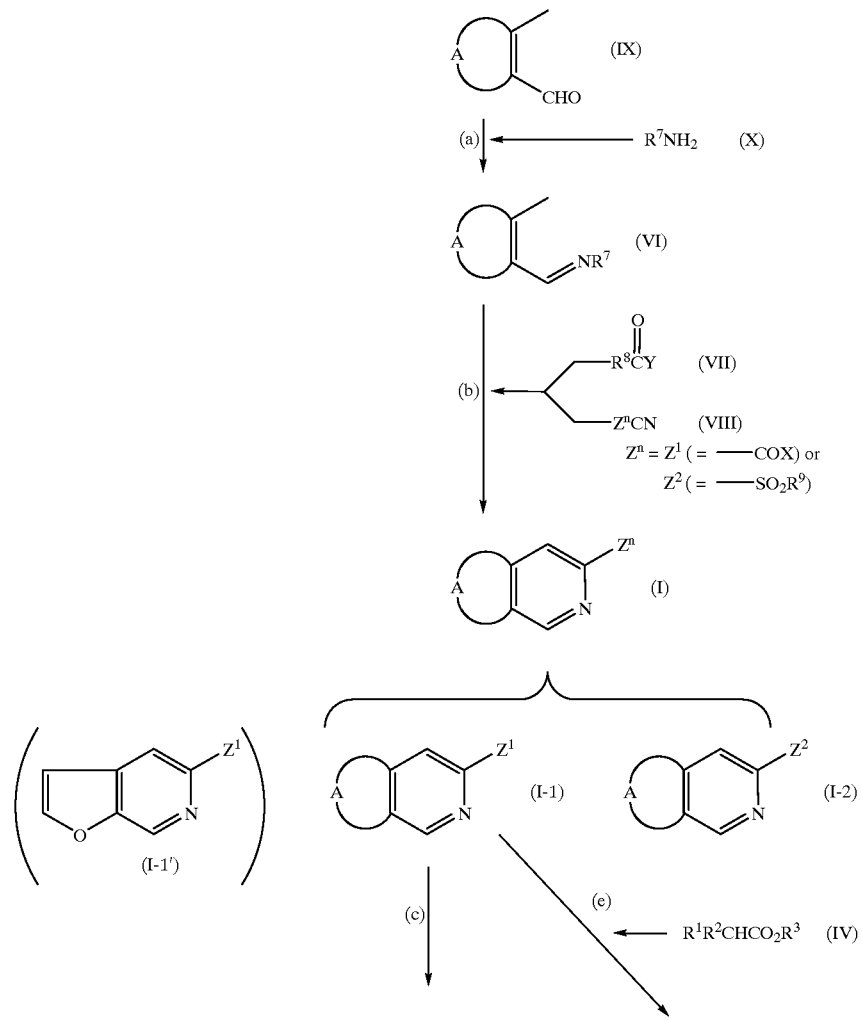

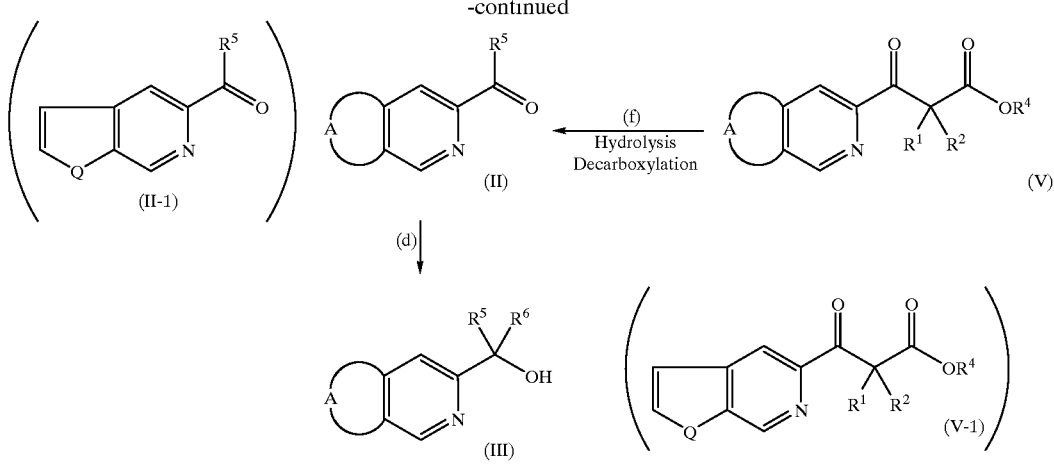

First, the substituents referred to in the General Formulas in the Reaction Scheme are explained below.

Specific examples of rings formed by A together with two bonded carbon atoms in the aforementioned general formula include 5-membered rings such as a dihydrofuran ring, a furan ring, a pyrrole ring, a pyrroline ring, a dehydrodioxolane ring, a pyrazole ring, a pyrazoline ring, an imidazole ring, an oxazole ring, an isooxazole ring, a thiazole ring, an oxadiazole ring, and a triazole ring; 6-membered rings such as a pyran ring, a dihydropyran ring, a pyridine ring, a dihydropyridine ring, a tetrahydropyridine ring, a dehydrodioxane ring, a dehydromorpholine ring, a pyridazine ring, a dihydropyridazine ring, a pyrimidine ring, a dihydropyrimidine ring, a tetrahydropyrimidine ring, a pyrazine ring, and a dihydropyrazine ring; 7-membered rings such as a thiazepine ring and various aza, oxa and thia substituted derivatives of a cycloheptene ring, a cycloheptadiene ring and a cycloheptatriene ring; and 8-membered rings such as various aza, oxa or thia substituted derivatives of a cyclooctene ring, a cyclooctadiene ring and a cyclooctatetraene ring.

Specific examples of condensed rings in cases where the ring formed by A together with two bonded carbon atoms forms a condensed ring with one or more other rings include a benzofuran ring, an isobenzofuran ring, a chromene ring, an indolizine ring, an indole ring, an isoindole ring, a quinolizine ring, an indazole ring, an isoquinoline ring, a phthalazine ring, a naphthylizine ring, a quinoxaline ring, a benzothiophene ring and their hydrogenated forms. Any of the above rings may be substituted.

Examples of alkoxyl groups represented by X or $R^8$ include linear or branched alkoxyl groups such as methoxy, ethoxy, propoxy, isopropoxy, butoxy, hexyloxy and octyloxy; and cycloalkyloxy groups such as cyclopropyloxy, cyclopentyloxy, and cyclohexyloxy. These alkoxyl groups and cycloalkyloxy groups may be substituted, where examples of such substituents include halogen atoms such as chlorine, bromine, iodine and fluorine; alkoxyl groups such as methoxy, ethoxy, propoxy and butoxy; hydroxyl group; nitro group; and aryl groups such as phenyl, p-methoxyphenyl and p-chlorophenyl.

Examples of alkenyloxy groups represented by X or $R^8$ include propenyloxy, butenyloxy and octenyloxy; examples of aryloxy groups include the phenyloxy; and examples of aralkyloxy groups include the benzyloxy. These alkenyloxy, aryloxy and aralkyloxy groups may be substituted, where examples of such substituents include halogen atoms such as chlorine, bromine, iodine and fluorine; alkoxyl groups such as methoxy, ethoxy, propoxy and butoxy; hydroxyl group; alkyl groups such as methyl, ethyl, propyl and butyl; tri-substituted silyloxy groups such as tert-butyldimethylsilyloxy and tert-butyldiphenylsilyloxy; nitro group; and aryl groups such as phenyl, p-methoxyphenyl and p-chlorophenyl.

Examples of organic groups represented by $R^9$ include alkyl groups such as methyl, ethyl, propyl, ter-butyl, octyl and dodecyl; aryl groups such as phenyl, tolyl, chlorophenyl, nitrophenyl and naphthyl; and aralkyl groups such as benzyl and nitrobenzyl.

Examples of hydrocarbon groups represented by $R^1$, $R^2$, $R^3$, $R^4$ and D include alkyl, alkenyl, aryl and aralkyl groups. Examples of alkyl groups include linear or branched alkyl groups such as methyl, ethyl, propyl, isopropyl, butyl, isobutyl, sec-butyl, tert-butyl, pentyl, isopentyl, neopentyl, hexyl, heptyl and octyl; and cycloalkyl groups such as cyclopropyl, cyclopentyl and cyclohexyl. These alkyl groups may be substituted, where examples of such substituents include halogen atoms such as chlorine, bromine, iodine and fluorine; alkoxyl groups such as methoxy, ethoxy, propoxy and butoxy; hydroxyl group; tri-substituted silyloxy groups such as tert-butyldimethylsilyloxy and tert-butyldiphenylsilyloxy; nitro group; and aryl groups such as phenyl, p-methoxyphenyl and p-chlorophenyl.

Examples of alkenyl groups include vinyl, propenyl, butenyl and octenyl; examples of aryl groups include phenyl; and examples of aralkyl groups include benzyl. These alkenyl, aryl, and aralkyl groups may be substituted, where examples of such substituents include halogen atoms such as chlorine, bromine, iodine and fluorine; alkoxyl groups such as methoxy, ethoxy, propoxy and butoxy; hydroxyl group; alkyl groups such as methyl, ethyl, propyl and butyl; tri-substituted silyloxy groups such as tert-butyldimethylsilyloxy and tert-butyldiphenylsilyloxy; nitro group; and aryl groups such as phenyl, p-methoxyphenyl and p-chlorophenyl.

Examples of alkyl groups represented by $R^5$, $R^6$, $R^7$ and $R^8$ include linear or branched alkyl groups such as methyl, ethyl, propyl, isopropyl, butyl, isobutyl, sec-butyl, tert-butyl, pentyl, isopentyl, neopentyl, hexyl, heptyl and octyl; and cycloalkyl groups such as cyclopropyl, cyclobutyl, cyclopentyl and cyclohexyl.

These alkyl groups may be substituted, where examples of such substituents include halogen atoms such as chlorine, bromine, iodine and fluorine; hydroxyl group; alkoxyl groups such as methoxy, ethoxy, propoxy and butoxy; tri-substituted silyloxy groups such as tert-butyldimethylsilyloxy and tert-butyldiphenylsilyloxy; nitro group; and aryl groups such as phenyl, p-methoxyphenyl and p-chlorophenyl.

Examples of alkenyl groups represented by $R^5$, $R^6$, $R^7$ and $R^8$ include vinyl, propenyl, butenyl and octenyl; examples of aryl groups include phenyl and naphthyl; and examples of aralkyl groups include benzyl. These alkenyl, aryl and aralkyl groups may be substituted, where examples of such substituents include halogen atoms such as chlorine, bromine, iodine and fluorine; hydroxyl group; alkyl groups such as methyl, ethyl, propyl and butyl; alkoxyl groups such as methoxy, ethoxy, propoxy and butoxy; tri-substituted silyloxy groups such as tert-butyldimethylsilyloxy and tert-butyldiphenylsilyloxy; nitro group; and aryl groups such as phenyl, p-methoxyphenyl, and p-chlorophenyl.

Examples of substitutable amino groups represented by $R^8$ include C1 to C8 linear or branched amino groups such as amino, dimethylamino, diethylamino, dipropylamino, diisopropylamino, dibutylamino, dihexylamino and dioctylamino.

These amino groups may be substituted by halogen atoms such as chlorine, bromine, iodine or fluorine; hydroxyl group; alkoxyl groups such as methoxy, ethoxy, propoxy or butoxy; tri-substituted silyloxy groups such as tert-butyldimethylsilyloxy and tert-butyldiphenylsilyloxy; nitro group; and phenyl, p-methoxyphenyl and p-chlorophenyl groups.

Examples of leaving groups represented by Y include halogen atoms such as chlorine, bromine and iodine, and acyloxy groups such as acetoxy, propionyloxy, butyryloxy and valeryloxy.

Production method of the present invention is described in each step in detail below.

Step (a): Step for producing an imine derivative VI by subjecting an aldehyde derivative IX and a primary amine X to dehydration condensation.

This conversion can be carried out in the same way as in methods commonly used to obtain an imine compound from an aldehyde and a primary amine. For example, the aldehyde derivative IX and the primary amine X are mixed in the presence or absence of a solvent and in the presence or absence of a dehydrating agent. Suitable solvents are those which give no undesired effect on the reaction, including aliphatic hydrocarbon solvents such as pentane, hexane, heptane and ligroin; aromatic hydrocarbon solvents such as benzene, toluene, xylene and chlorobenzene; ether solvents such as diethyl ether, tetrahydrofuran and dioxane; alcohol solvents such as methanol and ethanol; ester solvents such as methyl acetate, ethyl acetate and butyl acetate; or a mixture thereof. Suitable dehydrating agents include silica gel, molecular sieves, alumina, sodium sulfate, magnesium sulfate, copper sulfate, sodium hydroxide, or potassium hydroxide. The reaction can also be carried out in an azeotropic solvent with water while removing water by azeotropic dehydration.

Examples of the primary amines X include methylamine, ethylamine, propylamine, n-buthylamine, n-hexylamine, n-octylamine, aniline, p-chloroaniline, p-methoxyaniline, p-methylaniline and p-nitroaniline.

The resulting imine derivative VI is isolated and purified from the reaction mixture in the usual manner which commonly used in the isolation and purification of organic compounds. For example, the imine derivatives VI can be obtained by separating insoluble material contained in the reaction mixture by filtration, concentrating the filtrate and then purifying the residue by recrystallization, chromatography, or the like. The crude product can also be used without purification as such in subsequent reactions. When the imine derivative VI is precipitated from the reaction mixture, it is filtered, purified by recrystallization if necessary, and then can be used in the subsequent reaction.

Step (b): Step for producing a pyridine derivative I by reacting an imine derivative VI with a carbonylating agent VII and a nitrile VIII.

Examples of carbonylating agents VII include carboxylic anhydrides such as acetic anhydride, propionic anhydride, butyric anhydride, valeric anhydride and trifluoroacetic anhydride; carboxylic acid halides such as acetyl chloride, acetyl bromide, propionyl chloride, propionyl bromide, butyryl chloride, isobutyryl chloride, valeryl chloride, isovaleryl chloride, pivaloyl chloride, benzoyl chloride and benzoyl bromide; halogenoformic acid esters such as methyl chloroformate, ethyl chloroformate, propyl chloroformate, isopropyl chloroformate, butyl chloroformate, allyl chloroformate, phenyl chloroformate, nitrophenyl chloroformate and benzyl chloroformate; and carbamic acid halides such as N,N-dimethylcarbamyl chloride; among these chloroformic acid esters are preferred.

The amount of carbonylating agent VII may be used within a range of preferably 0.5 to 20 mol, and more preferably 1.1 to 10 mol, based on one mole of the imine derivative VI.

Examples of nitriles VIII include alkylsulfonylcyanides such as methanesulfonylcyanide, ethanesulfonylcyanide, propanesulfonylcyanide, butanesulfonylcyanide, tert-butanesulfonylcyanide, and dodecanesulfonylcyanide; arylsulfonylcyanides such as benzenesulfonylcyanide, toluenesulfonylcyanide, chlorobenzenesulfonylcyanide, nitrobenzenesulfonylcyanide and naphthalenesulfonylcyanide; aralkylsulfonylcyanides such as benzylsulfonylcyanide and nitrobenzylsulfonylcyanide; cyanoformic acid esters such as methyl cyanoformate, ethyl cyanoformate, propyl cyanoformate, isopropyl cyanoformate, butyl cyanoformate, allyl cyanoformate, phenyl cyanoformate, nitrophenyl cyanoformate and benzyl cyanoformate. The amount of nitrile VIII may be used within a range of preferably 0.5 to 20 mol, and more preferably 1.1 to 10 mol, based on one mole of the imine derivative VI.

The reaction can be carried out in the presence or absence of a solvent. The solvent is not particularly limited, provided that the reaction is not adversely affected, examples of which include aromatic hydrocarbons such as benzene, toluene, xylene, mesitylene and chlorobenzene; ethers such as tetrahydrofuran and dioxane; amides such as dimethyl formamide and 1-methyl-2-pyrrolidinone; and dimethyl sulfoxide. The amount of the solvent is not particularly limited, although it is usually used within a rage of preferably 1 to 200 times by weight based on the imine derivative VI.

The reaction temperature may vary, depending on the solvent, the carbonylating agent VII, and the nitrile VIII that is used, but is preferably within a range of 40° C. to the reflux temperature of the reaction system. The reaction can be carried out in a pressurized or reduced pressure state. The reaction time may vary, depending on the reaction temperature, but is usually rages from 30 minutes to 24 hours. The reaction time can be controlled by properly controlling the reaction temperature.

The reaction is carried out in the following manner, for example. That is, the carbonylating agent VII is added dropwise to a mixed solution of the nitrile VIII and the imine derivative VI within a temperature range from under ice cooling to the refluxing temperature of the reaction mixture, and after the completion of addition, the mixture is heated to the desired temperature until the imine derivative VI disappears.

The resulting pyridine derivative I is isolated and purified from the reaction mixture in the usual manner which commonly used in the isolation and purification of organic compounds. For example, after cooling the reaction mixture to room temperature, it is washed with sodium bicarbonate aqueous solution and saline water. Then, the solvent is distilled off, and the residue is purified by recrystallization, chromatography, or the like. When the product is precipitated from the reaction mixture, the reaction mixture can be cooled and then filtered with the addition of a poor solvent if necessary.

Step (c): Step for producing a pyridine carbonyl derivative II by reacting a pyridine ester derivative I-1 with a reducing agent, an alkylating agent, an alkenylating agent, an arylating agent or an aralkylating agent.

Examples of reducing agents include metal borohydrides such as sodium borohydride and lithium borohydride; and metal aluminum hydrides such as diisobutyl aluminum hydride, lithium aluminum hydride and sodium bismethoxyethoxyaluminum hydride. Examples of alkylating agents include alkyl metal compounds such as methyllithium, n-butyllithium, methylmagnesium chloride, methylmagnesium bromide, ethylmagnesium chloride and methylcerium chloride; examples of alkenylating agents include alkenyl metal compounds such as vinyllithium, vinylmagnesium chloride, allyllithium and allylmagnesium chloride; examples of arylating agents include aryl metal compounds such as phenyllithium and phenylmagnesium bromide; and examples of aralkylating agents include aralkyl metal compounds such as benzyllithium and benzylmagnesium bromide. The amount of reducing agent, the alkylating agent, the alkenylating agent, the arylating agent or the aralkylating agent may be used within a range of preferably 0.5 to 20 mol, and more preferably 1.1 to 2.0 mol, based on one mole of the pyridine ester derivative I-1.

The reaction can be carried out in the presence or absence of a solvent. The solvent is not particularly limited, provided that the reaction is not adversely affected, examples of which include ethers such as diethyl ether, diisopropyl ether, dibutyl ether, tetrahydrofuran, 1,2-diethoxyethane and diethylene glycol dimethyl ether; hydrocarbons such as hexane, benzene, toluene, xylene, mesitylene, and chlorobenzene; and amides such as 1-methyl-2-pyrrolidinone. The amount of solvent is not particularly limited, although it is usually used within a range of preferably 1 to 200 times by weight based on the pyridine ester derivative I-1.

The reaction temperature may vary, depending on the solvent, the reducing agent, the alkylating agent, the alkenylating agent, the arylating agent or the aralkylating agent that is used, but a temperature is usually preferred within a range of −100° C. to the refluxing temperature of the solvent. The reaction can be carried out in a pressurized or reduced pressure state. The reaction time also may vary, depending on the reaction temperature, but is usually range from 30 minutes to 24 hours. The reaction time can be controlled by properly controlling of the reaction temperature.

The resulting pyridine carbonyl derivative II is isolated and purified from the reaction mixture in the usual manner which commonly used in the isolation and purification of organic compounds. For example, after returning the reaction mixture to room temperature, it is then added to an acidic aqueous solution such as aqueous ammonium chloride and is hydrolyzed, it is then extracted with an organic solvent such as diethyl ether or ethyl acetate, the extract is washed with sodium bicarbonate aqueous solution and saline water, the solvent is distilled off, and the residue is purified by distillation, recrystallization, chromatography, or the like.

A pyridine alcohol derivative III in which $R^5$ and $R^6$ are a hydrogen atom can be obtained in a single stage when using a reducing agent with hydrogen as a nucleophilic agent, metal borohydrides such as sodium borohydride, lithium borohydride; and metal aluminum hydrides such as lithium aluminum hydride, sodium bismethoxyethoxyaluminum hydride.

Step (d): Step for producing a pyridine alcohol derivative III by reacting a pyridine carbonyl derivative II with a reducing agent, an alkylating agent, an alkenylating agent, an arylating agent or an aralkylating agent.

Examples of reducing agents include metal borohydrides such as sodium borohydride and lithium borohydride and metal aluminum hydrides such as diisobutyl aluminum hydride, lithium aluminum hydride, and sodium bismethoxyethoxyaluminum hydride. Reduction can also be carried out the use of hydrogen in the presence of a metal catalyst such as Raney nickel or Raney cobalt. Reduction by aluminum isopropoxide in isopropanol can also be adopted. The amount of the reducing agent may be used preferably within a range of 1.0 to 20 mol, and preferably 1.1 to 5 mol, based on one mole of the pyridine carbonyl derivative II.

Examples of alkylating agents include alkyl metal compounds such as methyllithium, n-butyllithium, methylmagnesium chloride, methylmagnesium bromide, ethylmagnesium chloride, and methylcerium chloride; examples of alkenylating agents include alkenyl metal compounds such as vinyllithium, vinylmagnesium chloride, allyllithium, and allylmagnesium chloride; examples of arylating agents include aryl metal compounds such as phenyllithium and phenylmagnesium bromide; and examples of aralkylating agents include aralkyl metal compounds such as benzyllithium and benzylmagnesium bromide. The amount of alkylating agent, the alkenylating agent, the arylating agent or the aralkylating agent may be used within a range of preferably 0.5 to 20 mol, and more preferably 1.1 to 2.0 mol, based on one mole of the pyridine carbonyl derivative II.

The reaction can be carried out in the presence or absence of a solvent. The solvent is not particularly limited, provided that the reaction is not adversely affected, examples of which include alcohols such as methanol, ethanol, propanol and isopropanol; ethers such as diethyl ether, diisopropyl ether, dibutyl ether, tetrahydrofuran, 1,2-diethoxyethane and diethylene glycol dimethyl ether; and hydrocarbons such as hexane, heptane, cyclohexane, benzene, toluene, and xylene. The amount of solvent is not particularly limited, although it is preferably used within a range of 1 to 200 times by weight based on the pyridine carbonyl derivative II.

The reaction temperature may vary, depending on the solvent, the reducing agent, the alkylating agent, the aralkylating agent that is used, but a temperature is preferred within a range of −100° C. to the refluxing temperature of the solvent. The reaction can be carried out in a pressurized or reduced pressure state. The reaction time also may vary, depending on the reaction temperature, but is usually range from 30 minutes to 24 hours. The reaction time can be controlled by properly controlling of the reaction temperature.

The resulting pyridine alcohol derivative III is isolated and purified from the reaction mixture in the usual manner which commonly used in the isolation and purification of organic compounds. For example, after returning the reaction mixture to room temperature, the reaction mixture is then added to an acidic aqueous solution such as aqueous ammonium chloride and is hydrolyzed, it is then extracted with an organic solvent such as diethyl ether or ethyl acetate, the extract is washed with sodium bicarbonate aqueous solution and saline water, the solvent is distilled off, and the residue is purified by distillation, recrystallization, chromatography, or the like.

Step (e): Step for producing a pyridine β-ketoester derivative V by reacting a pyridine ester derivative I-1 with an ester compound IV in the presence of a base.

Examples of bases include alkali metals such as sodium, lithium, and potassium; alkaline earth metals such as calcium; metal alcoholates such as sodium methoxide, sodium ethoxide, sodium propoxide, sodium isopropoxide, sodium butoxide, sodium tert-butoxide, sodium benzyloxide, potassium methoxide, potassium ethoxide, potassium propoxide, potassium isopropoxide, potassium butoxide and potassium tert-butoxide; organic magnesium halides such as methylmagnesium bromide, ethylmagnesium bromide, isopropylmagnesium bromide, and mesitylmagnesium bromide; metal hydrides such as sodium hydride and potassium hydride; and metal amides such as sodium amide, potassium amide, and lithium diisopropylamide. The amount of base is preferably used within a range of 0.5 to 10 mol, and more preferably 1 to 3 mol, based on one mole of the pyridine ester derivative I-1.

The ester compound IV is an ester compound derived from a carboxylic acid having a hydrogen atom in the alpha position, preferably an ester compound, such as a methyl ester, ethyl ester, propyl ester, isopropyl ester, butyl ester, isobutyl ester, 2-methylpropyl ester, tert-butyl ester, phenyl ester, benzyl ester, or chlorophenyl ester of a carboxylic acid such as acetic acid, propionic acid, butyric acid, isobutyric acid, 2-methylpropionic acid, valeric acid, isovaleric acid, caproic acid, or phenylacetic acid. Among these, aliphatic lower alcohol esters such as methyl esters, ethyl esters, propyl esters, isopropyl esters, butyl esters, isobutyl esters, 2-methylpropyl esters and tert-butyl esters are preferred.

The amount of ester compound IV is used preferably within a range of 0.5 to 10 mol, and more preferably 1 to 3 mol, based on one mole of the pyridine ester derivative I-1.

Although the reaction in this step can be carried out in the absence of a solvent, it is preferably carried out in the presence of a solvent.

Solvents are not particularly limited, provided that the reaction is not adversely affected, examples of which include aliphatic hydrocarbons such as pentane, hexane, cyclohexane, octane and ligroin; aromatic hydrocarbons such as benzene, toluene, xylene, cumene and mesitylene; ethers such as diethyl ether, tetrahydrofuran, and dioxane; polyethers such as ethylene glycol dimethyl ether, diethylene glycol dimethyl ether, triethylene glycol dimethyl ether, tetraethylene glycol dimethyl ether, ethylene glycol diethyl ether, diethylene glycol diethyl ether, triethylene glycol diethyl ether and tetraethylene glycol diethyl ether; and alcohols such as methanol, ethanol, propanol, isopropanol, butanol and t-butanol. Among these, the use of aromatic hydrocarbons, ethers, and polyethers as the solvent is preferred in view of the reaction rate, solubility of the pyridine derivative I, and the like. The amount of solvent is not particularly limited, provided that it is an amount allowing the pyridine ester derivative I-1 to dissolve under the reaction conditions, although it is preferably used within a range of 0.5 to 1000 times by weight, and more preferably 0.5 to 100 times by weight, based on the pyridine ester derivative I-1.

The reaction temperature is preferably within a range of 0 to 200° C., and more preferably 10 to 150° C.

The reaction in this step is not limited to any particular method, examples of which include: (1) mixing the prescribed amounts of the pyridine ester derivative I-1, the base, the ester compound IV and a solvent, and allowing the mixture to react at the prescribed temperature; (2) dissolving the prescribed amount of the pyridine ester derivative I-1 in a solvent, adding the base to the solution, heating the solution to the desired temperature, and then adding the ester compound IV all at once, intermittently or continuously, either as such or dissolved in a solvent; and (3) dissolving the prescribed amount of the base in the solvent, adding the ester compound IV to the solution, heating the solution to the desired temperature, and then adding the pyridine ester derivative I-1 all at once, intermittently, or continuously, either as such or dissolved in a solvent, to bring about the reaction.

The resulting pyridine β-ketoester derivative V can be readily isolated by neutralizing the reaction solution with the addition of an equivalent amount of acid relative to the base that was used, by then extracting the product with methylene chloride, toluene, xylene, benzene, chloroform, pentane, hexane, heptane or the like, and by concentrating the extract. Examples of acids which can be used for such purposes include carboxylic acids such as acetic acid and formic acid, and inorganic acids such as hydrochloric acid and sulfuric acid. The purity of the product can be increased by recrystallization, if necessary.

Under these reaction conditions, depending on the combination of the pyridine ester derivative I-1, the base, and the ester compound IV, as well as the proportions in which they are used, especially when using a metal alcoholate as the base or when using an alcohol as the solvent, a transesterification reaction sometimes progresses between the group represented by —X in the pyridine ester derivative I-1, the group represented by—$OR^3$ in the ester compound IV, the alcoholate moiety of the metal alcoholate and the alcohol. In such cases, the product can become a mixture of various types of moieties represented by —$OR^4$ in the pyridine β-ketoester derivative V, but the purity of such mixtures can be readily increased by common separation and purification means such as distillation, column chromatography, and recrystallization. These mixtures may also be used without any problems in the next step (f) for obtaining the pyridine carbonyl derivative II.

Step (f): Step for producing a pyridine carbonyl derivative II by hydrolysis and decarboxylation of a pyridine β-ketoester derivative V.

The amount of water that is used for hydrolysis is not particularly limited, although the use of at least one mole based on one mole of the pyridine β-ketoester derivative V is preferred in view of obtaining the target pyridine carbonyl derivative II with good yields, and no more than 100 mol water based on one mole of the pyridine β-ketoester derivative V is usually preferred in view of the reaction rate, the extraction efficiency following the reaction, the volume efficiency of the equipment, and the like.

Any common acid or base used in the hydrolysis of esters can be used in the hydrolysis reaction. Examples of acids include inorganic acids such as hydrochloric acid and sulfuric acid, and acidic gases such as hydrogen chloride gas can also be used. Examples of bases include alkali metal hydroxides such as sodium hydroxide and potassium hydroxide.

The intermediate product obtained by the hydrolysis of the pyridine β-ketoester derivative V is unstable under these reaction conditions, and the pyridine carbonyl derivative II is produced as a result of the rapid progress of the decarboxylation, thus allowing the decarboxylation to be carried out, usually at the same time as the hydrolysis, in the same reactor using the unmodified acid or base used in the hydrolysis. More acid or base can be added during the reaction to promote the hydrolysis and decarboxylation. The type of acid or base that is added at such times may be the same as, or different from, the acid or base initially used in the hydrolysis and decarboxylation. The amount of acid or base may be used within a range of preferably 0.001 to 100 mol, and more preferably 0.01 to 10 mol, based on one mole of the pyridine β-ketoester derivative V.

Methods for carrying out the reaction include methods in which the hydrolysis and decarboxylation are first started under basic conditions, and excess acid is added to the reaction system midway during the reaction to bring about acidic conditions, and methods in which the hydrolysis and decarboxylation are first started under acidic conditions, and excess base is added to the reaction system midway during the reaction to bring about basic conditions.

To obtain the pyridine carbonyl derivative II, a reaction mixture containing the pyridine β-ketoester derivative V is obtained by means of the reaction in step (e), and water and an acid or base are then added to the reaction solution without separating the pyridine β-ketoester derivative V from the reaction mixture to carry out the hydrolysis and decarboxylation in step (f), allowing the pyridine carbonyl derivative II to be obtained.

When the hydrolysis and decarboxylation in step (f) are then carried out without isolating the pyridine β-ketoester derivative V from the reaction mixture obtained in the reaction in step (e), the pyridine β-ketoester derivative V contained in the reaction mixture is quantified and analyzed, and the acid or base is used in an amount within the range described above relative to that amount. The amount of acid or base may be used within a range of preferably 0.001 to 100 mol, and more preferably 0.01 to 10 mol, based on one mole of the pyridine ester derivative I-1 used in step (e). The amount of water is used within a range of preferably 1 to 100 mol based on the amount of the pyridine β-ketoester derivative V contained in the reaction mixture. Water may also be used within a range of preferably 1 to 100 mol based on one mole of the pyridine ester derivative I-1.

Because a base is already present in the reaction mixture containing the pyridine β-ketoester derivative V obtained in step (e), the addition of water allows the existing base to act as a promoter in the hydrolysis and decarboxylation. In this embodiment, the neutralization in step (e) can be omitted.

The hydrolysis and decarboxylation may be carried out in the presence of an organic solvent. The type of organic solvent is not particularly limited, provided that the reaction is not adversely affected, examples of which include aliphatic hydrocarbons such as pentane, hexane, cyclohexane, octane and ligroin; aromatic hydrocarbons such as benzene, toluene, xylene, cumene and mesitylene; ethers such as diethyl ether, tetrahydrofuran and dioxane; polyethers such as ethylene glycol dimethyl ether, diethylene glycol dimethyl ether, triethylene glycol dimethyl ether, tetraethylene glycol dimethyl ether, ethylene glycol diethyl ether, diethylene glycol diethyl ether, triethylene glycol diethyl ether and tetraethylene glycol diethyl ether; and alcohols such as methanol, ethanol, propanol, isopropanol, butanol and t-butanol. Among these, the use of aromatic hydrocarbons, ethers and polyethers is preferred in view of the reaction rate, solubility of the pyridine β-ketoester derivative V, and the like. The amount of solvent is not particularly limited, although it is preferably used within a range of 0.5 to 100 weight parts based on the pyridine β-ketoester derivative V or the pyridine ester derivative I-1.

When the hydrolysis and decarboxylation in step (f) are then carried out without isolating the pyridine β-ketoester derivative V from the reaction mixture obtained in the reaction in step (e), the solvent used in step (e) can be used as such in step (f).

The reaction temperature is preferably within a range of 0 to 200° C., and more preferably 10 to 150° C.

The resulting pyridine carbonyl derivative II is isolated and purified from the reaction mixture in the usual manner which commonly used in the isolation and purification of organic compounds. For example, after cooling the reaction mixture to room temperature, it is extracted with an organic solvent such as methylene chloride, toluene, xylene, benzene, chloroform, pentane, hexane or heptane, the extract is washed with saline water, the solvent is distilled off, and the residue is purified by distillation, recrystallization, chromatography, or the like.

The pyridine carbonyl derivative II thus obtained can be converted to the corresponding pyridine alcohol derivative III by using the procedures in step (d).

Of the pyridine derivative represented by the General Formula I-2 contained the pyridine derivative I, for example, 5-benzenesulfonylfuro[2,3-c]pyridine can be converted to the intermediate noted in International Unexamined Patent Application WO 96/35678 by the following method, and a compound having antiviral activity can be derived by the method noted in the same application.

That is, 5-benzenesulfonylfuro[2,3-c]pyridine is converted to 5-cyanofuro[2,3-c]pyridine by reacting with an alkali metal cyanide. The cyanation can be carried out with or without a solvent. The solvent is not particularly limited, provided that the reaction is not adversely affected, examples of which include polar solvents such as dimethyl formamide, dimethyl sulfoxide, 1,3-dimethyl-2-imidazolidione. This reaction can also be carried out as a two-phase reaction using an phase-transfer catalyst. The reaction is carried out by heating 5-benzenesulfonylfuro[2, 3-c]pyridine and an excess amount of an alkali metal cyanide at a temperature within a range of room temperature to the reflux temperature. The resulting 5-cyanofuro[2,3-c] pyridine can be converted to 5-acetylfuro[2,3-c]pyridine by reacting with a methylating agent such as methyllithium or methylmagnesium chloride. The amount of the methylating agent is preferably within a range of 0.8 to 2 mol based on the starting pyridine derivative.

5-Acetylfuro[2,3-c]pyridine can be synthesized by reacting an acetyl anion equivalent with 5-benzenesulfonylfuro[2,3-c]pyridine, and then subsequent deprotection. Conventional acetyl anion equivalents can be used as the acetyl anion equivalent, although preferred examples include lactonitrile cyanhydrin ether, and acetyl anion equivalents prepared from an acetaldehyde thioacetal, thioacetal monoxide or the like and a strong base such as butyllithium, tert-butyllithium, methyllithium, phenyllithium, lithium diisopropylamide, lithium hexamethyldisilazide or sodium hexamethyldisilazide. The acetyl anion equivalent is preferably used in an amount of 0.8 to 2 mol based on one mole of the starting pyridine derivative.

The reaction may be carried out in a solvent that does not adversely affect the reaction, examples of such solvents preferably including ethers such as diethyl ether, tetrahydrofuran, dimethoxyethane and dioxane. The reaction temperature is preferably within the range of −40° C. to 100° C.

The resulting product is subsequently treated and deprotected by a common method, and the resulting 5-acetylfuro[2,3-c]pyridine can be converted to the intermediate by reduction with sodium borohydride, diisobutyl aluminum hydride, lithium aluminum hydride or the like noted in International Unexamined Patent Application WO 96/35678.

EXAMPLES

The present invention is described in further detail below with reference to examples, but the present invention is not limited in any way by these examples.

Example 1

3-Methylfuran-2-carbaldehyde (14.8 g, 0.135 mol) was mixed with hexane (50 mL), aniline (15.1 g, 0.162 mol) was added over 30 minutes at room temperature, and the mixture was heated to reflux for 4 hours with stirring. The mixture was allowed to cool to room temperature, and the solvent was then distilled off to give 28.1 g of the crude product of 3-methylfuran-2-carbaldehyde-N-phenylimine.

Benzenesulfonyl cyanide (90.2 g, 0.540 mol) and ethyl chloroformate (29.3 g, 0.270 mol) were mixed at room temperature in xylene (125 mL) and were stirred to reflux at a temperature of 120 to 140° C. A xylene (75 mL) solution of the crude 3-methylfuran-2-carbaldehyde-N-phenylimine (28.1 g) obtained above was added dropwise over 2 hours to the mixture. After all the solution had been added, the reaction mixture was heated to reflux for 3 hours, it was then cooled to room temperature, and the solvent was distilled off to give 81.3 g of crude product. This product was purified by column chromatography on silica gel, giving 17.2 g of 5-benzenesulfonylfuro[2,3-c]pyridine.

$^1$H-NMR spectra (270 MHz, CDCl$_3$, TMS, ppm) δ: 6.99 (1H, dd, J=2.16 Hz, 0.81 Hz), 7.49 to 7.62 (3H, m), 7.91 (1H, d, J=2.16 Hz), 8.07 to 8.11 (2H, m), 8.56 (1H, d, J=0.81 Hz), 8.90 (1H, s).

As is apparent from Example 1, the present invention can provide a method by which pyridine derivatives that are useful as intermediates for antiviral agents and the like can be produced with good yields in an industrially useful manner under moderate conditions.

Example 2

Ethyl cyanoformate (21.4 g, 0.216 mol) and 3-methylfuran-2-carbaldehyde-N-phenylimine (10.0 g, 54.1 mmol) were mixed at room temperature in xylene (50 mL) then heated to reflux at 120 to 140° C. with stirring. A xylene (30 mL) solution of 11.7 g (0.108 mol) of ethyl chloroformate was added dropwise for an hour to the resulting mixture. After all the solution had been added, the reaction mixture was heated to reflux for 2 hours, it was allowed to cool to room temperature, and the solvent was distilled off to give 14.0 g of crude product. This product was purified by column chromatography on silica gel, giving 5.40 g (52.3% yield) of 5-ethoxycarbonylfuro[2,3-c]pyridine.

$^1$H-NMR spectra (270 MHz, CDCl$_3$, TMS, ppm) δ: 1.47 (3H, t, J=7.16 Hz), 4.51 (2H, q, J=7.16 Hz), 6.94 (1H, dd, J=2.70 Hz, 1.08 Hz), 7.85 (1H, d, J=2.70 Hz), 8.50 (1H, d, J=1.08 Hz), 8.99 (1H, s).

Example 3 n-Butyl cyanoformate (13.7 g, 0.108 mol) and 3-methylfuran-2-carbaldehyde-N-phenylimine (5.0 g, 27.0 mmol) were mixed at room temperature in xylene (25 mL) then heated to reflux at 120 to 140° C. with stirring. A xylene (15 mL) solution of 7.40 g (54.2 mol) of n-butyl chloroformate was added dropwise for an hour to the resulting mixture. After all the solution had been added, the reaction mixture was heated to reflux for 2 hours, it was allowed to cool to room temperature, and the solvent was distilled off to give 7.10 g of crude product. This product was purified by column chromatography on silica gel, giving 2.71 g (45.8% yield) of 5-n-butoxycarbonylfuro[2,3-c]pyridine.

$^1$H-NMR spectra (270 MHz, CDCl$_3$, TMS, ppm) δ: 0.99 (3H, t, J=7.43 Hz), 1.49 (2H, tq, J=7.43 Hz), 1.84 (2H, tt, J=7.43 Hz), 4.45 (2H, t, J=7.43 Hz), 6.94 (1H, dd, J=2.43 Hz, J=0.81 Hz), 7.85 (1H, d, J=2.43 Hz), 8.48 (1H, d, J=0.81 Hz), 8.99 (1H, s).

Example 4

5-Ethoxycarbonylfuro[2,3-c]pyridine obtained in Example 2 (3.82 g, 20.0 mmol) was dissolved in tetrahydrofuran (50 mL) and cooled to −30° C. To the cooled solution, 22.0 mL (22.0 mol) of 1.0 M solution of methyllithium/diethyl ether was added, and the solution was stirred for 2 hours at the same temperature, the reaction mixture was then poured into 100 mL of 5% ammonium chloride aqueous solution which had been cooled on ice, and the product was extracted twice with 100 mL of ethyl acetate. After washing with 100 mL of saturated sodium bicarbonate aqueous solution and 100 mL of saturated saline water, the extract was concentrated to give 3.12 g of crude product. This product was purified by column chromatography on silica gel, giving 2.48 g (77.0% yield) of 5-acetylfuro[2,3-c]pyridine.

$^1$H-NMR spectra (270 MHz, CDCl$_3$, TMS, ppm) δ: 2.79 (3H, s), 6.94 (1H, dd, J=2.16 Hz, J=1.08 Hz), 7.83 (1H, d, J=2.16 Hz), 8.39 (1H, d, J=1.08 Hz), 8.91 (1H, s).

Example 5

5-Acetylfuro[2,3-c]pyridine obtained in Example 4 (2.42 g, 15.0 mmol) was dissolved in toluene (30 mL), and the solution was cooled to 0° C. To the cooled solution, 16.0 mL (16.0 mmol) of 1.0 M solution of diisobutyl aluminum hydride in toluene solution was added, and the solution was stirred for 2 hours at the same temperature, the reaction mixture was then poured into 100 mL of a 5% ammonium chloride aqueous solution which had been cooled on ice, and it was extracted twice with 100 mL of ethyl acetate. After washing with 100 mL of saturated sodium bicarbonate aqueous solution and 100 mL of saturated saline water, the extract was concentrated to give 2.36 g of crude product. This product was purified by column chromatography on silica gel, giving 2.25 g (92.0% yield) of 5-(1-hydroxyethyl)furo[2,3-c]pyridine.

As is apparent from Examples 2 to 5, the present invention can provide a method by which pyridine alcohol derivatives that are useful as intermediates for antiviral agents and the like can be produced with good yields in an industrially useful manner under moderate conditions. It also provides synthetic intermediates and a method of producing them giving such the method.

Example 6

5-Ethoxycarbonylfuro[2,3-c]pyridine obtained in Example 2 (956 mg, 5.0 mmol) was dissolved in 10 mL of toluene, 2.55 g (7.5 mmol) of a 20% ethanol solution of sodium ethoxide was added dropwise at room temperature to the solution, and 661 mg (7.5 mmol) of ethyl acetate was then added dropwise at room temperature with stirring. After all the ethyl acetate had been added, the reaction mixture was heated to 80° C., and a reaction was carried out for 8 hours. The reaction solution was then cooled to 5° C. and was neutralized with 450 mg (7.5 mmol) of acetic acid as the temperature was held 5–10° C., the solution was stirred for 30 minutes as the temperature was maintained, 1 mL of water was added, and the solution was returned to room temperature. The organic layer was separated, the aqueous layer was extracted twice with 5 mL of methylene chloride, and the combined organic layer was dried with anhydrous magnesium sulfate and then concentrated in a rotary evaporator to give 851 mg of solids. This solids were recrystallized from a mixed solvent of toluene-hexane, giving 769 mg (66% yield) of ethyl β-oxo-5-furo[2,3-c]pyridinepropionate in a purity of 99% by HPLC.

$^1$H-NMR spectra (270 MHz, CDCl$_3$, TMS, ppm) δ: 1.25 (3H, t, J=7.17 Hz), 4.21 (2H, q, J=7.17 Hz), 4.25 (2H, s), 6.95 (1H, d, J=2.46 Hz), 7.85 (1H, d, J=1.97 Hz), 8.42 (1H, s), 8.88 (1H, s).

Example 7

5-Ethoxycarbonylfuro[2,3-c]pyridine(956 mg, 5.0 mmol) was dissolved in 10 mL of toluene, 510 mg (7.5 mmol) of sodium ethoxide was added at room temperature to the solution, and 661 mg (7.5 mmol) of ethyl acetate was then added dropwise at room temperature with stirring. After all the ethyl acetate had been added, the reaction mixture was heated to 80° C., and a reaction was carried out for 4 hours. The reaction solution was then cooled to 5° C. and was neutralized with 450 mg (7.5 mmol) of acetic acid as the temperature was held 5–10° C., the solution was stirred for 30 minutes as the temperature was maintained, 1 mL water was then added, and the solution was returned to room temperature. The organic layer was separated, the aqueous layer was extracted twice with 5 mL of methylene chloride, and the combined organic layer was dried with anhydrous magnesium sulfate and then concentrated in a rotary evaporator, and the resulting solids were recrystallized from a mixed solvent of toluene-hexane, giving 840 mg (72% yield) of ethyl β-oxo-5-furo[2,3-c]pyridinepropionate in a purity of 99% by HPLC.

Example 8

As 510 mg (7.5 mmol) of sodium ethoxide was stirred in 5 mL toluene, 1.16 g (10.0 mmol) of t-butyl acetate was added dropwise at room temperature to the solution. Then, 956 mg (5.0 mmol) of 5-ethoxycarbonylfuro[2,3-c]pyridine dissolved in 5 mL of toluene was added dropwise at room temperature to the above solution. After all the solution had been added, the reaction mixture was heated to 60° C., and a reaction was carried out for 3 hours. The reaction solution was then cooled to 5° C. and was neutralized with 450 mg (7.5 mmol) of acetic acid as the temperature was held 5–10° C., the solution was stirred for 30 minutes as the temperature was maintained, 1 mL water was then added, and the solution was returned to room temperature. The organic layer was separated, the aqueous layer was extracted twice with 5 mL of methylene chloride, and the combined organic layer was dried with anhydrous magnesium sulfate and then concentrated in a rotary evaporator. The resulting solids were recrystallized from a mixed solvent of toluene-hexane mixture, giving 933 mg (80% yield) of ethyl β-oxo-5-furo[2,3-c]pyridinepropionate in a purity of 99% by HPLC.

Example 9

As 405 mg (7.5 mmol) of sodium methoxide was stirred in 5 mL toluene, 1.16 g (10.0 mmol) of t-butyl acetate was added dropwise at room temperature to the solution. Then, 956 mg (5.0 mmol) of 5-ethoxycarbonylfuro[2,3-c]pyridine was dissolved in 5 mL of toluene was added dropwise at room temperature to the above solution. After all the solution had been added, the reaction mixture was heated to 60° C., and a reaction was carried out for 3 hours. The reaction solution was then cooled to 5° C. and was neutralized with 450 mg (7.5 mmol) of acetic acid as the temperature was held 5–10° C., the solution was stirred for 30 minutes as the temperature was maintained, 1 mL water was then added, and the solution was returned to room temperature. The organic layer was separated, the aqueous layer was extracted twice with 5 mL of methylene chloride, and the combined organic layer was dried with anhydrous magnesium sulfate and then concentrated in a rotary evaporator to give 971 mg solids. NMR analysis revealed those to be a mixture of methyl β-oxo-5-furo[2,3-c]pyridinepropionate, ethyl β-oxo-5-furo[2,3-c]pyridinepropionate, and tert-butyl β-oxo-5-furo[2,3-c]pyridinepropionate (molar ratio of 55:44:1). The NMR spectra for the aforementioned ethyl β-oxo-5-furo[2,3-c]pyridinepropionate were consistent with those of the ethyl β-oxo-5-furo[2,3-c]pyridinepropionate obtained in Example 6.

Methyl β-oxo-5-furo[2,3-c]pyridinepropionate $^1$H-NMR spectra (270 MHz, CDCl$_3$, TMS, ppm) δ: 3.75 (3H, s), 4.29 (2H, s), 6.95 (1H, d, J=1.97 Hz), 7.85 (1H, d, J=1.98 Hz), 8.39 (1H, s), 8.88 (1H, s).

tert-Butyl β-oxo-5-furo[2,3-c]pyridinepropionate $^1$H-NMR spectra (270 MHz, CDCl$_3$, TMS, ppm) δ: 1.42 (9H, s), 4.13 (2H, s), 6.94 (1H, d, J=1.98 Hz), 7.83 (1H, d, J=1.98 Hz), 8.40 (1H, s), 8.88 (1H, s).

Example 10

The 971 mg of the mixture of methyl β-oxo-5-furo[2,3-c]pyridinepropionate, ethyl β-oxo-5-furo[2,3-c]pyridinepropionate, and tert-butyl β-oxo-5-furo[2,3-c]pyridinepropionate (molar ratio of 55:44:1) obtained in Example 9 was dissolved in 20 mL of toluene, and 1.04 g of 35% hydrochloric acid was added at room temperature with stirring. After addition, the reaction mixture was heated to 60° C., and a reaction was carried out for 3 hours with stirring. The reaction solution was then cooled to room temperature and was neutralized with 8.40 g of 5% sodium hydroxide aqueous solution. The organic layer was separated, the aqueous layer was extracted twice with 5 mL of methylene chloride, and the combined organic layer was dried with anhydrous magnesium sulfate and then concentrated in a rotary evaporator. The resulting solids were recrystallized from a mixed solvent of toluene-hexane, giving 629 mg of 5-acetylfuro[2,3-c]pyridine in a purity of 99% by HPLC (78% yield from 5-ethoxycarbonylfuro[2,3-c]pyridine).

Example 11

Ethyl β-oxo-5-furo[2,3-c]pyridinepropionate(1.17 g, 5.0 mmol) was dissolved in 20 mL of toluene, and 1.5 mL (7.5 mmol) of 10 N sulfuric acid was added at room temperature with stirring. After addition, the reaction mixture was heated to 80° C., and a reaction was carried out for 6 hours with stirring. The solution was then cooled to room temperature and neutralized with 12 mL of 5% sodium hydroxide aqueous solution. The organic layer was separated, the aqueous layer was extracted twice with 5 mL of methylene chloride, and the combined organic layer was dried with anhydrous magnesium sulfate and then concentrated in a rotary evaporator. The resulting solids were recrystallized from a mixed solvent of toluene-hexane, giving 580 mg of 5-acetylfuro[2,3-c]pyridine in a purity of 99% by HPLC (72% yield).

Example 12

Ethyl β-oxo-5-furo[2,3-c]pyridinepropionate (583 mg, 2.5 mmol) obtained in Example 7 was dissolved in 10 mL of toluene, and 3 g of 10% sodium hydroxide aqueous solution was added with stirring. After addition, the reaction mixture was heated to 60° C., and a reaction was carried out for 8 hours with stirring. It was then cooled to room temperature, the organic layer was separated, the aqueous layer was extracted twice with 5 mL of methylene chloride, and the combined organic layer was dried with anhydrous magnesium sulfate and then concentrated in a rotary evaporator. The resulting solids were recrystallized from a mixed solvent of toluene-hexane, giving 205 mg (51% yield) of 5-acetylfuro[2,3-c]pyridine in a purity of 99% by HPLC.

Example 13

As 405 mg (7.5 mmol) of sodium methoxide was stirred in 5 mL of toluene, 1.16 g (10.0 mmol) of tert-butyl acetate was added dropwise at room temperature to the solution. Then, 956 mg (5.0 mmol) of 5-ethoxycarbonylfuro[2,3-c]pyridine dissolved in 5 mL of toluene was added dropwise at room temperature to the above solution. After all the solution had been added, the reaction mixture was heated to 60° C., a reaction was carried out for 3 hours. The resulting reaction mixture was then neutralized with 450 mg (7.5 mmol) of acetic acid, the solution was stirred for 30 minutes, 1.5 mL (7.5 mmol) of 5 N hydrochloric acid was then added, and the solution was stirred for 5 hours at 60° C. to carry out a reaction. The solution was then returned to room temperature, the organic layer was separated, the aqueous layer was extracted twice with 5 mL of methylene chloride, and the combined organic layer was dried with anhydrous magnesium sulfate and then concentrated in a rotary evaporator. The resulting solids were recrystallized from a mixed solvent of toluene-hexane, giving 580 mg (72% yield) of 5-acetylfuro[2,3-c]pyridine in a purity of 99% by HPLC.

Example 14

5-Acetylfuro[2,3-c]pyridine (2.42 g, 15.0 mmol) obtained by the method in Example 13 was dissolved in toluene (30 mL), and the solution was cooled to 0° C. To the cooled solution, 16.0 mL (16.0 mmol) of 1.0 M solution of diisobutyl aluminum hydride in toluene was added, and the solution was stirred for 2 hours at this temperature, the reaction mixture was then poured into 100 mL of a 5% ammonium chloride aqueous solution which had been cooled on ice, and it was extracted twice with 100 mL of ethyl acetate. The extract was washed with 100 mL of saturated sodium bicarbonate aqueous solution and 100 mL of saturated saline water, and the solvent was concentrated to give 2.36 g of crude product. This product was purified by column chromatography on silica gel, giving 2.25 g (92.0% yield) of 5-(1-hydroxyethyl)furo[2,3-c]pyridine.

$^1$H-NMR spectra (270 MHz, CDCl$_3$, TMS, ppm) δ: 1.55 (3H, s), 4.03 (1H, s), 4.99 (1H, q, J=5.93 Hz), 6.80 (1H, d, J=1.98 Hz), 7.53 (1H, s), 7.77 (1H, d, J=2.47 Hz), 8.80 (1H, s).

As is apparent from Examples 6 to 14, the present invention can provide methods by which pyridine derivatives that are useful as intermediates for antiviral agents and the like can be produced with good yields in an industrially useful manner under moderate conditions. It also provides synthetic intermediates and methods of producing them giving such the methods.

The entire disclosure of the specifications, claims and summaries of Japanese Patent Applications No. 9-291075 filed on Oct. 23, 1997, No. 10-64862 filed on Mar. 16, 1998 and No. 10-219943 filed Aug. 4, 1988 is herein incorporated by reference.

What is claimed is:

1. A pyridine carbonyl derivative represented by General Formula II-1

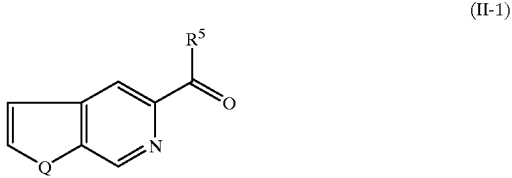

(II-1)

where R$^5$ represents a hydrogen atom, —CHR$^1$R$^2$, or an alkenyl group, an aryl group or an aralkyl group which may be substituted; R$^1$ and R$^2$ each independently represent a hydrogen atom or a hydrocarbon group which may be substituted; Q represents a divalent group selected from —O—, and —S—.

2. A compound according to claim 1 where Q is —O—.
3. A compound according to claim 1 where Q is —S—.

* * * * *

UNITED STATES PATENT AND TRADEMARK OFFICE
CERTIFICATE OF CORRECTION

PATENT NO. : 6,111,111
DATED : August 29, 2000
INVENTOR(S) : Hideki Matsuda, et al.

It is certified that error appears in the above-identified patent and that said Letters Patent is hereby corrected as shown below:

Title page,
Item [30], the 2nd Foreign Application Priority Data, is listed incorrectly. Item [30] should read as follows:

[30] Foreign Application Priority Data

Oct. 23, 1997 [JP] Japan................................ 9-291075
Mar. 16, 1998 [JP] Japan............................ 10-064862
Aug. 4, 1998 [JP] Japan............................ 10-219943

Signed and Sealed this

Second Day of October, 2001

Attest:

NICHOLAS P. GODICI
Attesting Officer   Acting Director of the United States Patent and Trademark Office